United States Patent
Liu et al.

(10) Patent No.: US 10,692,283 B2
(45) Date of Patent: Jun. 23, 2020

(54) GEOMETRIC MODEL ESTABLISHMENT METHOD BASED ON MEDICAL IMAGE DATA

(71) Applicant: NEUBORON MEDTECH LTD., Nanjing, Jiangsu (CN)

(72) Inventors: Yuanhao Liu, Jiangsu (CN); Peiyi Lee, Jiangsu (CN)

(73) Assignee: NEUBORON MEDTECH LTD., Nanjing, Jiangsu (CN)

(*) Notice: Subject to any disclaimer, the term of this patent is extended or adjusted under 35 U.S.C. 154(b) by 59 days.

(21) Appl. No.: 15/967,774

(22) Filed: May 1, 2018

(65) Prior Publication Data
US 2018/0247452 A1  Aug. 30, 2018

Related U.S. Application Data

(63) Continuation of application No. PCT/CN2016/102335, filed on Oct. 18, 2016.

(30) Foreign Application Priority Data

Nov. 17, 2015 (CN) .......................... 2015 1 0790248

(51) Int. Cl.
 *G06T 17/30* (2006.01)
 *G06T 7/11* (2017.01)
 (Continued)

(52) U.S. Cl.
 CPC ............ *G06T 17/30* (2013.01); *G06T 7/0012* (2013.01); *G06T 7/11* (2017.01); *G06T 7/13* (2017.01);
 (Continued)

(58) Field of Classification Search
 None
 See application file for complete search history.

(56) References Cited

U.S. PATENT DOCUMENTS 5,341,292 A   8/1994  Zamenhof
5,873,830 A * 2/1999  Hossack ............ G01S 7/52046
                                                    600/447

FOREIGN PATENT DOCUMENTS

CN   101458826 A   6/2009
CN   104267425 A   1/2015
(Continued)

OTHER PUBLICATIONS

International Search Report of PCT/CN2016/102335, dated Jan. 11, 2017.
(Continued)

*Primary Examiner* — Jason A Pringle-Parker
(74) *Attorney, Agent, or Firm* — Locke Lord LLP; Tim Tingkang Xia, Esq.

(57) ABSTRACT

Provided is a geometric model establishment method based on medical image data, including: a step of reading medical image data; a step of defining a tissue type by a conversion relationship between the medical image data and the tissue type; a step of deciding the number of tissue clusters; a step of defining a tissue density by a conversion relationship between the medical image data and the density; a step of establishing 3D encoding matrix with information about the tissue and the density; and a step of generating a geometric model. According to a conversion relationship between medical image data and a tissue type, the number of tissue clusters can be determined according to actual requirements, so that the tissue type, the element composition and the density are provided more accurately, and an established geometric model is better matched to the real situation reflected by the medical image data.

6 Claims, 3 Drawing Sheets

(51) Int. Cl.
    *G06T 7/168*     (2017.01)
    *G06T 7/13*     (2017.01)
    *G06T 7/00*     (2017.01)
    *G06T 17/00*     (2006.01)
    *A61N 5/10*     (2006.01)

(52) U.S. Cl.
    CPC ............ *G06T 7/168* (2017.01); *A61N 5/103* (2013.01); *A61N 2005/109* (2013.01); *G06T 17/00* (2013.01); *G06T 2200/08* (2013.01); *G06T 2207/10081* (2013.01); *G06T 2207/10088* (2013.01); *G06T 2207/30096* (2013.01); *G06T 2210/32* (2013.01)

(56) References Cited

FOREIGN PATENT DOCUMENTS

| | | |
|---|---|---|
| EP | 1658878 A1 | 5/2006 |
| EP | 2815789 A1 | 12/2014 |
| WO | 2006138513 A1 | 12/2006 |

OTHER PUBLICATIONS

D. R. White et al., Photon, Electron, Proton and Neutron Interaction Data for Body Tissues, Journal of the International Commission on Radiation Units and Measurements, 1992.

Barbara Vanderstraeten et al., Conversion of CT numbers into tissue parameters for Monte Carlo dose calculations: a multi-centre study, Physics in Medicine and Biology, 2007, 52, 539-562.

\* cited by examiner

GEOMETRIC MODEL ESTABLISHMENT METHOD BASED ON MEDICAL IMAGE DATA

RELATED APPLICATION INFORMATION

This application is a continuation of International Application No. PCT/CN2016/102335, filed on Oct. 18, 2016, which claims priority to Chinese Patent Application No. 201510790248.7, filed on Nov. 17, 2015, the disclosures of which are hereby incorporated by reference.

FIELD OF THE DISCLOSURE

The present disclosure relates generally to a geometric model establishment method, and, more particularly, to geometric model establishment method based on medical image data.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}$B)-containing pharmaceuticals have high neutron capture cross section and produces $^4$He and $^7$Li heavy charged particles through $^{10}$(n,α)$^7$Li neutron capture and nuclear fission reaction. The total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

Three-dimensional model is widely used in scientific experiment analysis, scientific experiment simulation field. For example, in the field of nuclear radiation and protection, in order to simulate the dose absorbed by the human body under certain radiation conditions, it is often necessary to process the medical image data by using computer technology to establish an accurate lattice model required by MCNP and combine with MCNP (Monte Carlo Program) for simulation.

At present, the Monte Carlo method is a tool that can accurately simulate the collision trajectory and energy distribution of the nuclear particle in the three-dimensional space of the irradiated target. The combination of the Monte Carlo method with a complex three-dimensional human anatomy model represents a leap forward of simulation in computer technology. In diagnostic radiographic examination, accurate human organ dose assessment is very beneficial for radiation therapy. At present around the world, a variety of human models have been successfully established and combined with Monte Carlo simulation program to evaluate the accuracy of the human body's absorbed dose in the radiation environment. It is a prerequisite for Monte Carlo simulation to successfully transform the three-dimensional anatomical model of human body into geometric description required by Monte Carlo program. It is also the hot and difficult point of Monte Carlo simulation in the world at present.

Medical image data such as Magnetic Resonance Imaging (MRI) or Computed Tomography (CT) can provide detailed tissue geometry information specific for human body features and provide data basis for physical modeling of human internal structures. In the field of neutron capture therapy, it is an important issue how to establish the geometric model required by MCNP based on medical image data. In other words, how to build the lattice model required by the MCNP software input file based on the medical image data so as to improve the accuracy of the treatment plan.

Therefore, it is necessary to propose a method of establishing a geometric model needed for MCNP based on medical image data to improve the accuracy of treatment plan.

The statements in this section merely provide background information related to the present disclosure and may not constitute prior art.

SUMMARY

One aspect of the present disclosure is to provide a geometric model establishment method based on medical image data, the method including the steps of: reading medical image data; defining a tissue type by a conversion relationship between the medical image data and the tissue type; deciding the number of tissue clusters; defining a tissue density by a conversion relationship between the medical image data and the tissue density; establishing 3D encoding matrix with information about the tissue and the density; and generating a geometric model.

According to a conversion relationship between medical image data and a tissue type, the number of tissue clusters can be determined according to actual requirements, so that the tissue type, the element composition and the density are provided more accurately, and an established geometric model is better matched to the real situation reflected by the medical image data.

Implementations of this aspect may include one or more of the following features.

More particularly, the geometric model establishment method is used for neutron capture therapy and further includes a step of assigning a B-10 concentration and a step of establishing a 3D encoding matrix with B-10 concentration information. The geometric model labeled with B-10 concentration information clearly shows that the concentration of the boron-containing drug in each tissue and then when performing neutron capture therapy simulation, it is more realistic to reflect the actual situation.

The number of the tissue clusters is the number of the tissue clusters manually defined by the user plus the four tissue clusters or fourteen tissue clusters already existing in the database. If there is no established corresponding number of the tissue clusters in the existing database, a new number of the tissue clusters can be defined by the user. This avoids the situation where only approximate choices can be made if the corresponding number of the tissue clusters cannot be exactly matched in an existing database, thereby effectively improving the accuracy of the modeling.

More preferably, the geometric model establishment method further includes a step of establishing a 3D tissue encoding matrix and a step of establishing a 3D density encoding matrix. According to the slice of the medical image data, the corresponding tissue encoding and density encoding are established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

Another aspect of the present disclosure is to provide a geometric model establishment method based on medical image data, the method including the steps of: reading medical image data; defining or reading an ROI boundary; determining whether a medical image voxel is within an ROI boundary; if yes, then proceeding to a step of manually defining a tissue type and density by assigning a particular tissue and density to voxels within each ROI boundary or proceeding to a step of automatically defining a ROI tissue type and density by a conversion relationship between the medical image data and the tissue type/density, if no, then proceeding to a step of automatically defining a tissue type by a conversion relationship between the medical image data and the tissue type, and defining a tissue density by a conversion relationship between the medical image data and the density; establishing 3D encoding matrix with information about the tissue and the density; and generating a geometric model.

The so-called ROI is the region of interest (hereinafter collectively referred to as ROI), the user can manually define the tissue type, elemental composition and density of ROI. If the medical image voxel is not within the ROI boundary, the definition of the tissue type is performed according to the conversion relationship between the medical image data and the tissue type, and the number of tissue clusters is determined according to the actual needs so as to provide the tissue type, the element composition and the density more accurately, and the established geometric model more closely matches the real situation reflected by the medical image data.

More particularly, the geometric model establishment method is applied to neutron capture therapy, and the geometric model establishment method further includes a step of assigning a B-10 concentration and a step of establishing a 3D encoding matrix with B-10 concentration information. The geometric model labeled with B-10 concentration information clearly shows that the concentration of the boron-containing drug in each tissue and then when performing neutron capture therapy simulation, it is more realistic to reflect the actual situation.

The number of the tissue clusters is the number of the tissue clusters manually defined by the user plus the four tissue clusters or fourteen tissue clusters already existing in the database. If there is no established corresponding number of the tissue clusters in the existing database, a new number of the tissue clusters can be defined by the user. This avoids the situation where only approximate choices can be made if the corresponding number of the tissue clusters cannot be exactly matched in an existing database, thereby effectively improving the accuracy of the modeling.

More preferably, the geometric model establishment method further includes a step of establishing a 3D tissue encoding matrix and a step of establishing a 3D density encoding matrix. According to the slice of the medical image data, the corresponding tissue encoding and density encoding are established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

The medical image data may be Magnetic Resonance Imaging (MRI) or Computed Tomography (CT). The following examples will be described based on the data of Computed Tomography (CT). The file format of the CT is usually DICOM. However, it is well known to those skilled in the art that other medical image data can also be used as long as the medical image data can be converted into an MCNP lattice model with tissue type, density, and B-10 concentration information, it can be applied to the geometric model establishment method based on the medical image data disclosed in the present disclosure.

The beneficial effects and/or features in the embodiments of the present disclosure are as follows:

1. The tissue type, elemental composition and density of the region of interest (ROI) are manually defined;
2. For non-ROI CT image voxels, tissue type matching can be performed automatically, and according to the difference in CT values, an existing database can distinguish tissues consisted of four or fourteen different elements, and the tissue consisted of other numbers of different elements can also be determined according to actual experimental results;
3. It is difficult to assign a unique tissue density for ROIs with CT values covering a wide range, such as mucosal chamber, and the user can automatically convert the CT values to tissue/density according to the methods disclosed in the embodiments of the present disclosure;
4. The method disclosed by the embodiments of the present disclosure automatically compiles the B-10 element into all the voxels after inputting parameters such as a boron-containing drug concentration in normal blood, a tissue/tumor-blood boron concentration ratio, and the like;
5. The final resulting three-dimensional MCNP lattice model will have information on the tissue type (elemental composition), density, and B-10 concentration.

Further areas of applicability will become apparent from the description provided herein. It should be understood that the description and specific examples are intended for purposes of illustration only and are not intended to limit the scope of the present disclosure.

DETAILED DESCRIPTION

The embodiments of the present disclosure are further described in detail below with reference to the accompanying drawings, so that those skilled in the art can implement the technical solutions according to the description.

More preferably, a geometric model establishment method based on medical image data for neutron capture therapy is taken as an embodiment of the present disclosure. The following will briefly introduce neutron capture therapy, especially boron neutron capture therapy.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n)$^7$Be and $^9$Be (p, n) $^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

Figure 1:
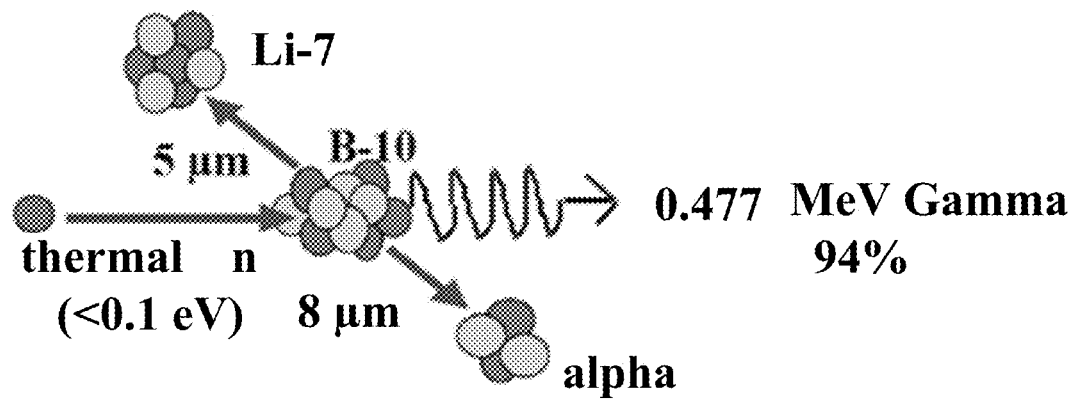
FIG. 1 is a schematic view of boron neutron capture reaction.
Figure 2:
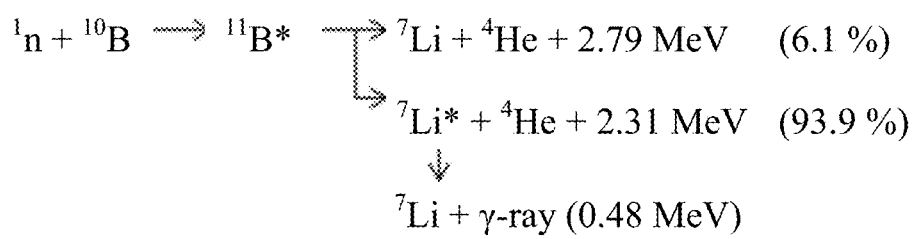
FIG. 2 is a nuclear reaction formula of $^{10}B\ (n,\alpha)^{7}Li$ neutron capture.

BNCT takes advantage that the boron ($^{10}$B)-containing pharmaceuticals have high neutron capture cross section and produces $^4$He and $^7$Li heavy charged particles through $^{10}$B(n,α)$^7$Li neutron capture and nuclear fission reaction. As illustrated in FIGS. 1 and 2, a schematic drawing of BNCT and a nuclear reaction formula of $^{10}$B (n,α)$^7$Li neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

The purpose of the embodiments of the present disclosure is to convert medical image data into an MCNP lattice model with tissue type, density and B-10 concentration information for tissue dose simulation calculation of boron neutron capture therapy. The medical image data may be Magnetic Resonance Imaging (MRI) or Computed Tomography (CT). The following examples will be described based on the data of Computed Tomography (CT). The file format of the CT is usually DICOM. However, it is well known to those skilled in the art that other medical image data can also be used as long as the medical image data can be converted into an MCNP lattice model with tissue type, density, and B-10 concentration information, it can be applied to the geometric model establishment method based on the medical image data disclosed in the present disclosure.

Briefly, the geometric model establishment method based on medical image data disclosed by the embodiments of the present disclosure mainly includes the following processes:
1. The computer tomography (DICOM format) is input, and CT images will be presented on the corresponding interface;
2. The defined ROI boundary is automatically read, and a new ROI can also be added;
3. The software will determine the location of each voxel on the CT image and classify all voxels as "falling within the ROI boundary" and "falling outside the ROI boundary";
4. For the voxels inside the ROI boundary, according to the actual needs, the relative tissue type and tissue density for each ROI can be manually defined by a user, or the CT value can be automatically matched with the tissue type and density, so as to avoid the error of dose calculation because of assigning unique tissue type (elemental composition) and density of ROI which covers a wide range of CT values (e.g. mucosal chamber).
5. For the voxels outside the ROI boundary, the tissue type is automatically defined, and it can be distinguished into four or fourteen tissues consisted of different elements according to the difference of the CT values, and the user may choose to use the four tissues listed in the ICRU-46 Report Form, as detailed below, or the fourteen tissues consisting of different elements published in 2007 by Vanderstraeten et al., as detailed below, depending on the actual judgment;
6. For the voxel of which the density has not been manually defined, the density will be assigned automatically according to the difference of the CT values, and a total of 96 density clusters can be distinguished;
7. The user manually inputs parameters such as a boron-containing drug concentration in normal blood, a tumor-blood boron concentration ratio, a tissue-blood boron concentration ratio and the like, and compiles the B-10 element into all the voxels;
8. The software will integrate the information such as the tissue type (elemental composition), tissue density, tissue B-10 concentration and the like to generate three-dimensional MCNP lattice model, and compile a lattice card, a cell card, a surface card, and a material card in MCNP input file format.

Figure 3:
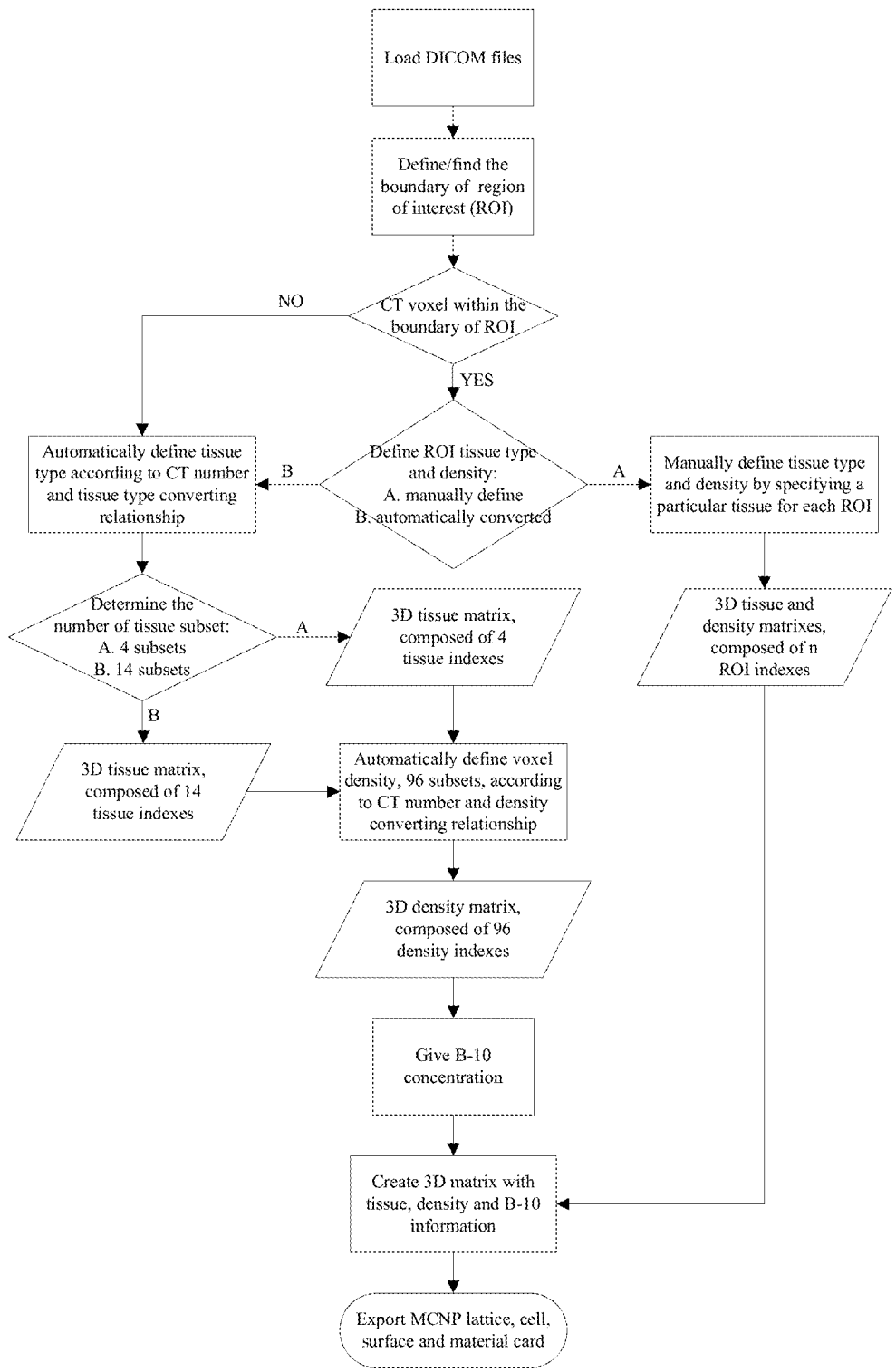
FIG. 3 is a logic diagram of a geometric model establishment method based on medical image data according to an embodiment of the present disclosure.

Specifically, referring to FIG. 3, the geometric model establishment method based on medical image data disclosed by the present disclosure includes two embodiments.

One aspect of the present disclosure is to provide a geometric model establishment method based on medical image data, the method including the steps of: reading medical image data; defining a tissue type by a conversion relationship between the medical image data and the tissue type; deciding the number of tissue clusters; defining a tissue density by a conversion relationship between the medical image data and the tissue density; establishing 3D encoding matrix with information about the tissue and the density; and generating a geometric model.

According to a conversion relationship between medical image data and a tissue type, the number of tissue clusters can be determined according to actual requirements, so that the tissue type, the element composition and the density are provided more accurately, and an established geometric model is better matched to the real situation reflected by the medical image data.

More particularly, the geometric model establishment method is used for neutron capture therapy and further includes a step of assigning a B-10 concentration and a step of establishing a 3D encoding matrix with B-10 concentration information. The geometric model labeled with B-10 concentration information clearly shows that the concentration of the boron-containing drug in each tissue and then when performing neutron capture therapy simulation, it is more realistic to reflect the actual situation.

The number of the tissue clusters is the number of the tissue clusters manually defined by the user plus the four tissue clusters or fourteen tissue clusters already existing in the database. If there is no established corresponding number of the tissue clusters in the existing database, a new number of the tissue clusters can be defined by the user. This avoids the situation where only approximate choices can be made if the corresponding number of the tissue clusters cannot be exactly matched in an existing database, thereby effectively improving the accuracy of the modeling.

More preferably, the geometric model establishment method further includes a step of establishing a 3D tissue encoding matrix and a step of establishing a 3D density encoding matrix. According to the slice of the medical image data, the corresponding tissue encoding and density encoding are established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

Another aspect of the present disclosure is to provide a geometric model establishment method based on medical image data, the method including the steps of: reading medical image data; defining or reading an ROI boundary; determining whether a medical image voxel is within an ROI boundary; if yes, then proceeding to a step of manually defining a tissue type and density by assigning a particular tissue and density to voxels within each ROI boundary or proceeding to a step of automatically defining a ROI tissue type and density by a conversion relationship between the medical image data and the tissue type/density, if no, then proceeding to a step of automatically defining a tissue type by a conversion relationship between the medical image data and the tissue type, and defining a tissue density by a conversion relationship between the medical image data and the density; establishing 3D encoding matrix with information about the tissue and the density; and generating a geometric model.

The so-called ROI is the region of interest (hereinafter collectively referred to as ROI), the user can manually define the tissue type, elemental composition and density of ROI. If the medical image voxel is not within the ROI boundary, the definition of the tissue type is performed according to the conversion relationship between the medical image data and the tissue type, and the number of tissue clusters is determined according to the actual needs so as to provide the tissue type, the element composition and the density more accurately, and the established geometric model more closely matches the real situation reflected by the medical image data.

More particularly, the geometric model establishment method is applied to neutron capture therapy, and the geometric model establishment method further includes a step of assigning a B-10 concentration and a step of establishing a 3D encoding matrix with B-10 concentration information. The geometric model labeled with B-10 concentration information clearly shows that the concentration of the boron-containing drug in each tissue and then when performing neutron capture therapy simulation, it is more realistic to reflect the actual situation.

The number of the tissue clusters is the number of the tissue clusters manually defined by the user plus the four tissue clusters or fourteen tissue clusters already existing in the database. If there is no established corresponding number of the tissue clusters in the existing database, a new number of the tissue clusters can be defined by the user. This avoids the situation where only approximate choices can be made if the corresponding number of the tissue clusters cannot be exactly matched in an existing database, thereby effectively improving the accuracy of the modeling.

More preferably, the geometric model establishment method further includes a step of establishing a 3D tissue encoding matrix and a step of establishing a 3D density encoding matrix. According to the slice of the medical image data, the corresponding tissue encoding and density encoding are established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

The medical image data may be Magnetic Resonance Imaging (MRI) or Computed Tomography (CT). The following examples will be described based on the data of Computed Tomography (CT). The file format of the CT is usually DICOM. However, it is well known to those skilled in the art that other medical image data can also be used as long as the medical image data can be converted into an MCNP lattice model with tissue type, density, and B-10 concentration information, it can be applied to the geometric model establishment method based on the medical image data disclosed in the present disclosure.

Figure 4:
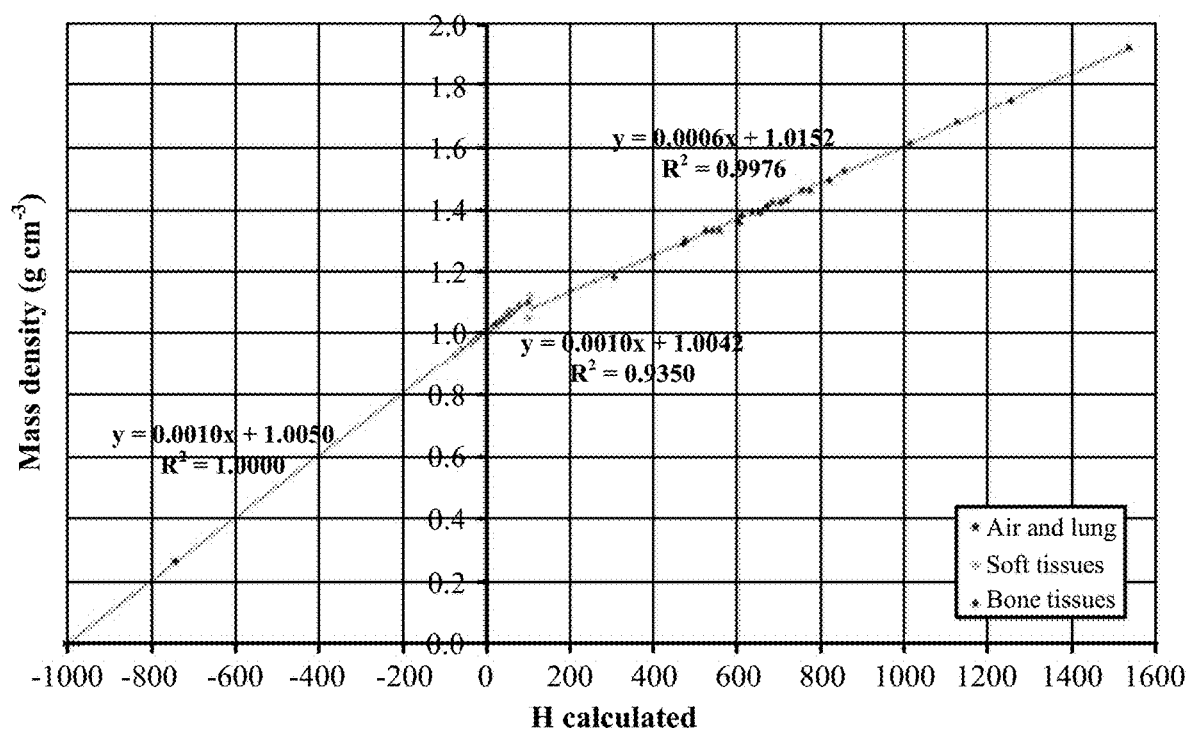
FIG. 4 is a chart showing regression curve formula and correlation coefficient of CT value (HU) and tissue density.

Referring to FIG. 4, the CT value—tissue type and the CT value—Tissue density conversion chart in the existing database in the geometric model establishment method based on medical image data disclosed in the present disclosure will be described below.

The CT value, also known as Hounsfield Unit (HU), is the unit of reaction light attenuation coefficient, which is defined as formula 1:

$$H = 1000\left(\frac{\mu}{\mu_{water}} - 1\right) \qquad \text{Formula 1}$$

Reference was made to the literature published by Vanderstraeten et al. in 2007 (Barbara Vanderstraeten et al, "Conversion of CT numbers into tissue parameters for Monte Carlo dose calculations: a multi-center study", Phys. Med. Biol. 52 (2007) 539-562.), depending on the CT values, they can be converted into one type of air, one type of lung, two types of soft tissues (adipose and muscle) and ten types of bones, in other words, different CT values correspond to a total of 14 tissues consisted of different elements, as shown in Table 1 below.

TABLE 1 different CT values correspond to a total of 14 tissues consisted of
different elements (weight percentage of element)

| tissue | HU | H | C | N | O | Na | Mg | P | S | Cl | Ar | K | Ca |
|---|---|---|---|---|---|---|---|---|---|---|---|---|---|
| air | <−900 | | | 75.5 | 23.2 | | | | | | 1.3 | | |
| lung | −900~−100 | 10.3 | 10.5 | 3.1 | 74.9 | 0.2 | | 0.2 | 0.3 | 0.3 | | 0.2 | |
| adipose | −100~20 | 11.2 | 53.3 | 1.1 | 34.1 | 0.1 | | | 0.1 | 0.1 | | | |
| muscle | 20~100 | 10.1 | 15.6 | 4.0 | 69.3 | 0.3 | | 0.1 | 0.3 | 0.2 | | 0.1 | |
| bone | 100~250 | 9.5 | 45.3 | 2.5 | 35.5 | 0.1 | | 2.1 | 0.2 | 0.1 | | 0.1 | 4.6 |
| bone | 250~400 | 8.4 | 40.1 | 2.8 | 36.9 | 0.1 | 0.1 | 3.6 | 0.2 | 0.1 | | 0.1 | 7.7 |
| bone | 400~550 | 7.5 | 35.5 | 3.0 | 38.1 | 0.1 | 0.1 | 4.8 | 0.2 | 0.1 | | 0.1 | 10.5 |
| bone | 550~700 | 6.7 | 31.6 | 3.3 | 39.2 | 0.1 | 0.1 | 5.9 | 0.2 | 0.1 | | | 12.8 |
| bone | 700~850 | 6.0 | 28.1 | 3.5 | 40.1 | 0.1 | 0.1 | 6.8 | 0.2 | | | | 14.9 |
| bone | 850~1000 | 5.3 | 25.0 | 3.7 | 41.0 | 0.1 | 0.1 | 7.7 | 0.3 | | | | 16.8 |
| bone | 1000~1150 | 4.8 | 22.3 | 3.8 | 41.7 | 0.1 | 0.2 | 8.4 | 0.3 | | | | 18.4 |
| bone | 1150~1300 | 4.3 | 19.8 | 4.0 | 42.3 | 0.1 | 0.2 | 9.1 | 0.3 | | | | 19.9 |
| bone | 1300~1450 | 3.8 | 17.6 | 4.1 | 42.9 | 0.1 | 0.2 | 9.7 | 0.3 | | | | 21.2 |
| bone | >1450 | 3.4 | 15.6 | 4.2 | 43.5 | 0.1 | 0.2 | 10.3 | 0.3 | | | | 22.4 |

Reference was made to Report No. ICRU-46 (International Commission on Radiation Units and Measurements, Photon, electron, proton and neutron interaction data for body tissues, ICRU-46, Tech. Rep., 1992.), and four major human brain tissues were taken, including air, adult brain, adult skin and cranium, with the corresponding density and elemental composition shown in Table 2.

TABLE 2 different CT values correspond to a total of 4 tissues consisted of different
elements (weight percentage of element)

| tissue | $\rho$ (g/cm³) | H | C | N | O | Na | Mg | P | S | Cl | Ar | K | Ca |
|---|---|---|---|---|---|---|---|---|---|---|---|---|---|
| air | 0.001293 | | | 75.5 | 23.2 | | | | | | 1.3 | | |
| adult brain | 1.04 | 10.7 | 14.5 | 2.2 | 71.2 | 0.2 | | 0.4 | 0.2 | 0.3 | | 0.3 | |
| adult skin | 1.09 | 10.0 | 20.4 | 4.2 | 64.5 | 0.2 | | 0.1 | 0.2 | 0.3 | | 0.1 | |
| cranium | 1.61 | 5.6 | 21.2 | 4.0 | 43.5 | 0.1 | 0.2 | 8.1 | 0.3 | | | | 17.6 |

The same reference was made to the literature of Vanderstraeten et al., which unified the true experimental values from hospitals, and sorted out the relationship formula of CT value corresponding to tissue density, as shown in FIG. 4; the geometric model establishment method based on medical image data disclosed in the present disclosure used the three sets of regression formulas in FIG. 4 to classify CT values (−1000 to 2000) into 96 density clusters, as shown in Table 3.

TABLE 3

CT value and mass density conversion. $HU_L$ and $HU_U$ are the lower and
upper limits of the CT value, respectively

| $HU_L$ | $HU_U$ | $\rho$ (g/cm³) |
|---|---|---|
| | −990 | 0.0050 |
| −990 | −980 | 0.0200 |
| −980 | −970 | 0.0300 |
| −970 | −960 | 0.0400 |
| −960 | −950 | 0.0500 |
| −950 | −925 | 0.0675 |
| −925 | −900 | 0.0925 |
| −900 | −875 | 0.1175 |
| −875 | −850 | 0.1425 |
| −850 | −825 | 0.1675 |
| −825 | −800 | 0.1925 |
| −800 | −775 | 0.2175 |
| −775 | −750 | 0.2425 |
| −750 | −725 | 0.2675 |
| −725 | −700 | 0.2925 |

TABLE 3-continued

CT value and mass density conversion. $HU_L$ and $HU_U$ are the lower and
upper limits of the CT value, respectively

| $HU_L$ | $HU_U$ | $\rho$ (g/cm³) |
|---|---|---|
| −700 | −650 | 0.3300 |
| −650 | −600 | 0.3800 |
| −600 | −550 | 0.4300 |
| −550 | −500 | 0.4800 |
| −500 | −450 | 0.5300 |
| −450 | −400 | 0.5800 |
| −400 | −350 | 0.6300 |
| −350 | −300 | 0.6800 |
| −300 | −250 | 0.7300 |
| −250 | −200 | 0.7800 |
| −200 | −175 | 0.8175 |
| −175 | −150 | 0.8425 |
| −150 | −125 | 0.8675 |
| −125 | −100 | 0.8925 |
| −100 | −80 | 0.9142 |
| −80 | −60 | 0.9342 |
| −60 | −40 | 0.9542 |
| −40 | −20 | 0.9742 |
| −20 | 0 | 0.9942 |
| 0 | 20 | 1.0142 |
| 20 | 40 | 1.0342 |
| 40 | 60 | 1.0542 |
| 60 | 80 | 1.0742 |
| 80 | 100 | 1.0942 |
| 100 | 125 | 1.0827 |
| 125 | 150 | 1.0977 |
| 150 | 175 | 1.1127 |

TABLE 3-continued

CT value and mass density conversion. $HU_L$ and $HU_U$ are the lower and upper limits of the CT value, respectively

| $HU_L$ | $HU_U$ | ρ (g/cm³) |
|---|---|---|
| 175 | 200 | 1.1277 |
| 200 | 225 | 1.1427 |
| 225 | 250 | 1.1577 |
| 250 | 275 | 1.1727 |
| 275 | 300 | 1.1877 |
| 300 | 325 | 1.2027 |
| 325 | 350 | 1.2177 |
| 350 | 375 | 1.2327 |
| 375 | 400 | 1.2477 |
| 400 | 425 | 1.2627 |
| 425 | 450 | 1.2777 |
| 450 | 475 | 1.2927 |
| 475 | 500 | 1.3077 |
| 500 | 525 | 1.3227 |
| 525 | 550 | 1.3377 |
| 550 | 575 | 1.3527 |
| 575 | 600 | 1.3677 |
| 600 | 625 | 1.3827 |
| 625 | 650 | 1.3977 |
| 650 | 675 | 1.4127 |
| 675 | 700 | 1.4277 |
| 700 | 725 | 1.4427 |
| 725 | 750 | 1.4577 |
| 750 | 775 | 1.4727 |
| 775 | 800 | 1.4877 |
| 800 | 825 | 1.5027 |
| 825 | 850 | 1.5177 |
| 850 | 875 | 1.5327 |
| 875 | 900 | 1.5477 |
| 900 | 925 | 1.5627 |
| 925 | 950 | 1.5777 |
| 950 | 975 | 1.5927 |
| 975 | 1000 | 1.6077 |
| 1000 | 1050 | 1.6302 |
| 1050 | 1100 | 1.6602 |
| 1100 | 1150 | 1.6902 |
| 1150 | 1200 | 1.7202 |
| 1200 | 1250 | 1.7502 |
| 1250 | 1300 | 1.7802 |
| 1300 | 1350 | 1.8102 |
| 1350 | 1400 | 1.8402 |
| 1400 | 1450 | 1.8702 |
| 1450 | 1500 | 1.9002 |
| 1500 | 1550 | 1.9302 |
| 1550 | 1600 | 1.9602 |
| 1600 | 1650 | 1.9902 |
| 1650 | 1700 | 2.0202 |
| 1700 | 1750 | 2.0502 |
| 1750 | 1800 | 2.0802 |
| 1800 | 1850 | 2.1102 |
| 1850 | 1900 | 2.1402 |
| 1900 | 1950 | 2.1702 |
| 1950 | 2000 | 2.2002 |
| 2000 | | 2.2152 |

The beneficial effects and/or features in the embodiments of the present disclosure are as follows:
1. The tissue type, elemental composition and density of the region of interest (ROI) are manually defined;
2. For non-ROI CT image voxels, tissue type matching can be performed automatically, and according to the difference in CT values, an existing database can distinguish tissues consisted of four or fourteen different elements, and the tissue consisted of other numbers of different elements can also be determined according to actual experimental results;
3. It is difficult to assign a unique tissue density for ROIs with CT values covering a wide range, such as mucosal chamber, and the user can automatically convert the CT values to tissue/density according to the methods disclosed in the embodiments of the present disclosure;
4. The method disclosed by the embodiments of the present disclosure automatically compiles the B-10 element into all the voxels after inputting parameters such as a boron-containing drug concentration in normal blood, a tissue/tumor-blood boron concentration ratio, and the like;
5. The final resulting three-dimensional MCNP lattice model will have information on the tissue type (elemental composition), density, and B-10 concentration.

While illustrative embodiments of the disclosure have been described above in order to provide a person of ordinary skill in the art with an understanding of the disclosure, it should be clear that the disclosure is not to be limited in scope by the specific embodiments. It will be apparent to those skilled in the art that as long as the various changes are within the spirit and scope of the disclosure as defined and determined by the appended claims, they are obvious and are within the scope of the disclosure as claimed.

What is claimed is:

1. A geometric model establishment method based on medical image data, the method comprising the steps of:
   reading medical image data;
   defining a tissue type of a tissue by a conversion relationship between the medical image data and tissue types;
   determining a quantity of tissue clusters of the tissue, wherein the quantity of the tissue clusters of the tissue is a quantity of the tissue clusters manually defined by a user plus a quantity of four tissue clusters or fourteen tissue clusters already existing in a database;
   defining a tissue density of the tissue by a conversion relationship between the medical image data and tissue density values;
   establishing a 3D encoding matrix with information about the tissue and the tissue density; and
   generating a geometric model based on the 3D encoding matrix.

2. The geometric model establishment method based on medical image data according to claim 1, wherein the geometric model establishment method is used for neutron capture therapy and further comprises a step of assigning a B-10 concentration and a step of establishing the 3D encoding matrix with B-10 concentration information.

3. The geometric model establishment method based on medical image data according to claim 1, wherein the geometric model comprises a lattice card, a cell card, a surface card and a material card required by an input file of MCNP (Monte Carlo Program) software.

4. A geometric model establishment method based on medical image data, the method comprising the steps of:
   reading medical image data;
   defining or reading a region of interest (ROI) boundary;
   determining whether each of a plurality of medical image voxels in the medical image data is within the ROI boundary;
   when one of the medical image voxels is determined to be within the ROI boundary, proceeding to a step of manually defining a tissue type and a tissue density of a tissue by assigning a particular tissue and the tissue density to the one of the medical image voxels within the ROI boundary or proceeding to a step of automatically defining the tissue type and the density of the tissue by a conversion relationship between the medical image data and tissue types and a conversion relationship between the medical image data and density values,
   when one of the medical image voxels is determined not to be within the ROI boundary, proceeding to a step of automatically defining the tissue type of the tissue by the conversion relationship between the medical image data and the tissue types, and defining the tissue density of the tissue by the conversion relationship between the medical image data and the density values;

determining a quantity of tissue clusters of the tissue, wherein the quantity of the tissue clusters of the tissue is a quantity of the tissue clusters manually defined by a user plus a quantity of four tissue clusters or fourteen tissue clusters already existing in a database;

establishing a 3D encoding matrix with information about the tissue and the tissue density; and generating a geometric model based on the 3D encoding matrix.

5. The geometric model establishment method based on medical image data according to claim 4, wherein the geometric model establishment method is used for neutron capture therapy and further comprises a step of assigning a B-10 concentration and a step of establishing the 3D encoding matrix with B-10 concentration information.

6. The geometric model establishment method based on medical image data according to claim 4, wherein the geometric model comprises a lattice card, a cell card, a surface card and a material card required by an input file of MCNP (Monte Carlo Program) software.

* * * * *